(12) United States Patent
Sodickson et al.

(10) Patent No.: US 9,897,573 B2
(45) Date of Patent: Feb. 20, 2018

(54) SYSTEM, METHOD AND COMPUTER-ACCESSIBLE MEDIUM FOR PROVIDING GENERALIZED LOCAL MAXWELL TOMOGRAPHY FOR MAPPING OF ELECTRICAL PROPERTY GRADIENTS AND TENSORS

(71) Applicant: New York University, New York, NY (US)

(72) Inventors: Daniel K. Sodickson, Larchmont, NY (US); Dmitry S. Novikov, New York, NY (US); Leeor Alon, New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 14/782,401

(22) PCT Filed: Apr. 7, 2014

(86) PCT No.: PCT/US2014/033176
§ 371 (c)(1),
(2) Date: Oct. 5, 2015

(87) PCT Pub. No.: WO2014/176023
PCT Pub. Date: Oct. 30, 2014

(65) Prior Publication Data
US 2016/0054262 A1 Feb. 25, 2016

Related U.S. Application Data

(60) Provisional application No. 61/809,195, filed on Apr. 5, 2013.

(51) Int. Cl.
*G01R 29/12* (2006.01)
*G01N 27/60* (2006.01)
(Continued)

(52) U.S. Cl.
CPC ............ *G01N 27/60* (2013.01); *G01R 33/48* (2013.01); *G01R 33/246* (2013.01)

(58) Field of Classification Search
CPC .. G01R 33/246; G01R 33/48; G01R 33/1215; G01N 27/60; G01N 24/08; A61B 5/0536; A61B 5/055
(Continued)

(56) References Cited

U.S. PATENT DOCUMENTS

| | | |
|---|---|---|
| 6,522,910 B1 | 2/2003 | Gregory |
| 2009/0264791 A1 | 10/2009 | Gregory et al. |
| 2012/0146637 A1 | 6/2012 | Zhu et al. |

OTHER PUBLICATIONS

Sodickson, D.K., et. al. "From Artifact to State of the Art: An Introduction to Electromagnetic Tissue Property Mapping" ISMRM, 387; 2012.
(Continued)

*Primary Examiner* — An Do
(74) *Attorney, Agent, or Firm* — Andrews Kurth Kenyon LLP

(57) ABSTRACT

Exemplary system, method, and computer-accessible medium can be provided for determining at least one property (e.g., an electrical property or a cross-section property) of at least one target. For example, it is possible to determine electromagnetic-field-related quantities associated with signals provided from the target(s). The electromagnetic-field-related quantities can be provided to procedures to relate the electromagnetic-field-related quantities to a plurality of unknown electrical property values and residual field-related unknown values of the target(s). The property(ies) of the target(s) can be determined by determining the plurality of unknown electrical property values and residual field-related unknown values of the target(s).

16 Claims, 11 Drawing Sheets

(51) Int. Cl.
*G01R 33/48* (2006.01)
*G01R 33/24* (2006.01)

(58) Field of Classification Search
USPC .................. 324/307, 457, 458; 600/427, 428
See application file for complete search history.

(56) References Cited

OTHER PUBLICATIONS

Geddes, L. A. & Baker, L. E. "The specific resistance of biological material—a compendium of data for the biomedical engineer and physiologist." Med Biol Eng 5, 271-293; 1967.

Gabriel, S., et al. "The dielectric properties of biological tissues: II. Measurements in the frequency range 10 Hz to 20 GHz." Phys Med Biol 41, 2251-2269; 1996.

**Joines, W. et al "The measured electrical properties of normal and malignant human tissues from 50 to 900 MHz." Med Phys 21, 547-550; 1994.

Metherall, P., et al. "Three-dimensional electrical impedance tomography." Nature 380, 509-512; 1996.

Lauterbur, P. "Image formation by induced local interactions: examples employing nuclear magnetic resonance." Nature 242, 190-191; 1973.

**Katscher, U. et al. "Determination of electric conductivity and local SAR via B1 mapping." IEEE Trans Med Imaging 28, 1365-1374; 2009.

**Katscher, U., et al. B(1) -based specific energy absorption rate determination for nonquadrature radiofrequency excitation. Magn Reson Med, 68, 1911-1918; 2012.

Zhang, X., et al. "Complex B(1) mapping and electrical properties imaging of the human brain using a 16-channel transceiver coil at 7T." Magn Reson Med, 69, 1285-1296; 2013.

**Hoult, D. I. The Principle of Reciprocity in Signal Strength Calculations—A Mathematical Guide. Concepts Magn Reson 12, 173-187; 2000.

International Serach Report for International Application No. PCT/US2014/033176 dated Mar. 2, 2015.

Written Opinion for International Application No. PCT/US2014/033176 dated Mar. 2, 2015.

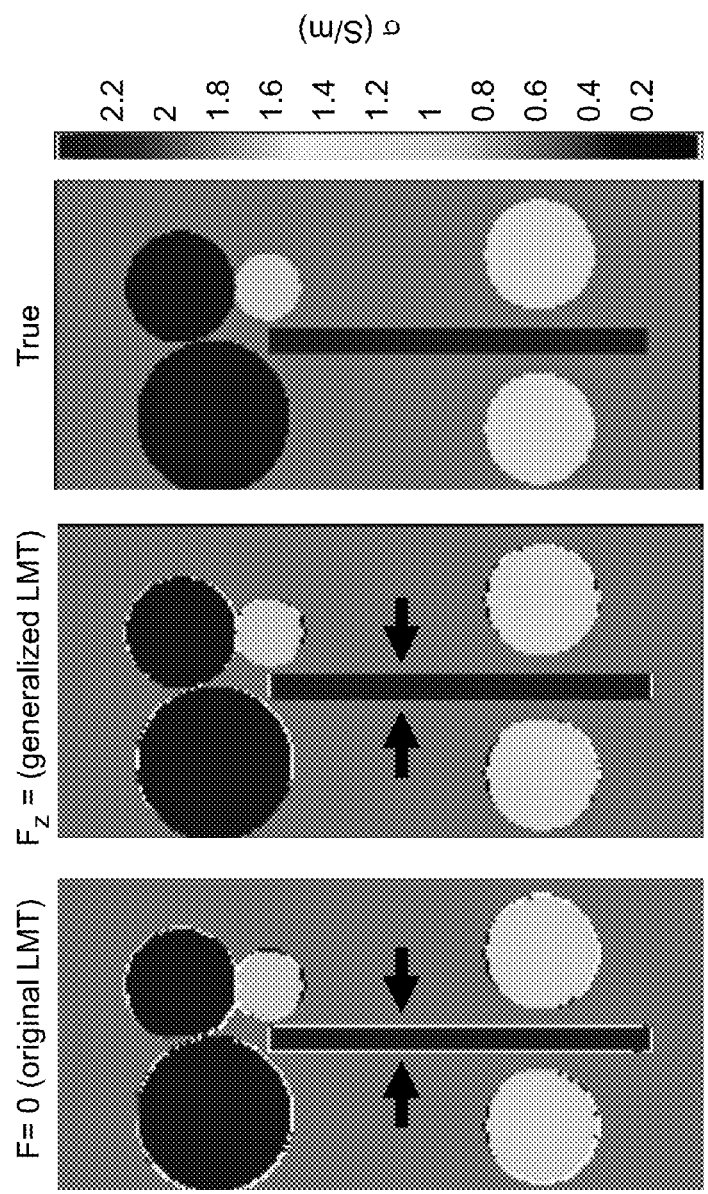

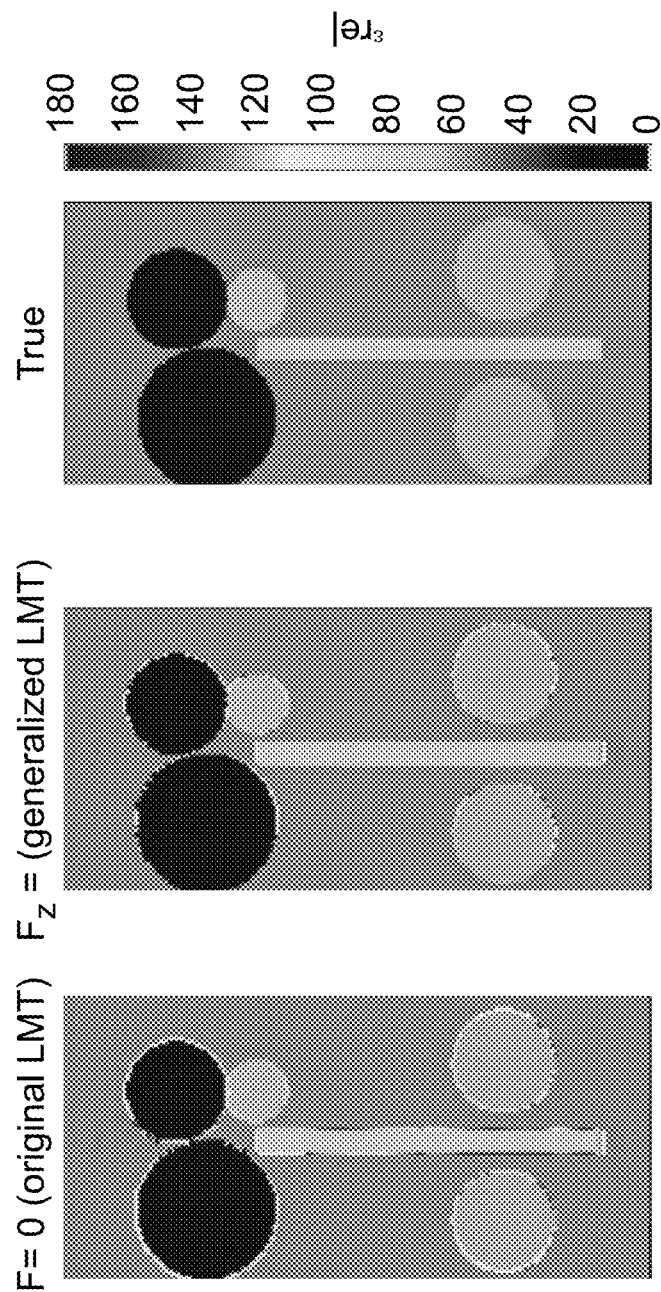

SYSTEM, METHOD AND COMPUTER-ACCESSIBLE MEDIUM FOR PROVIDING GENERALIZED LOCAL MAXWELL TOMOGRAPHY FOR MAPPING OF ELECTRICAL PROPERTY GRADIENTS AND TENSORS

CROSS-REFERENCE TO RELATED APPLICATION

This application relates to and claims the benefit and priority from International Patent Application No. PCT/US2014/033176 filed on Apr. 7, 2014, which relates to U.S. patent application Ser. No. 13/314,105, filed on Dec. 7, 2011, the entire disclosures of which are incorporated herein by reference. The present disclosure also relates to and claims priority from U.S. Patent Application No. 61/809,195 filed on Apr. 5, 2013, the entire disclosure of which is incorporated herein by reference.

FIELD OF THE DISCLOSURE

The present disclosure relates to the mapping of electrical properties of tissues or materials, and more specifically, relates to exemplary systems, methods, computer-accessible mediums and, frameworks for facilitating noninvasive mapping of electrical properties of tissue or materials.

BACKGROUND INFORMATION

Electrical conductivity and permittivity has been the subject of intensive study in the physical and biological sciences. Extensive experimental studies and theoretical discoveries in physics and materials science have surrounded the microscopic origins of electrical conductivity and permittivity. Biological tissue has long been recognized as an electrically active medium. Given the critical importance of electrical signal transduction in physiology, interest in bioelectrical properties has been ongoing. Thus, knowledge of the internal distribution of these electrical properties in intact materials and organisms can advance fundamental understandings, promote new discoveries, and facilitate novel diagnostics and interventions in a diverse array of fields.

Despite all of this active interest, attempts to map the spatial distribution of electrical properties, in vivo, in intact human organs, or even heterogeneous materials have met with limited success. Attempts to map electrical properties noninvasively have struggled with underlying instability and ill-posedness. Typically, either invasive probes have been used, which can disturb the local environment and preclude true cross-sectional mapping, or alternatively, "electrical prospection" approaches such as Electrical Impedance Tomography ("EIT") have been devised in which surface-based measurements can be converted to property maps via notoriously ill-posed inverse problems. EIT, and similar techniques, have been deployed for diagnosis or surveillance of disease, but fundamental limitations in resolution and robustness have thus far impeded widespread use.

Accurate volumetric maps of electrical properties in situ can be of interest not only for basic biophysical understanding of tissue and material structure, but also for a wide array of applications in human health. Tumors, for example, can be known to have markedly different electrical properties from normal tissue. Brain, heart, and muscle are all electrical organs, with the ability to carry current and store charge being fundamental to their operation, and with derangements in these functions being associated with disease processes ranging from epilepsy to arrhythmia to myopathy. Various interventions, such as transcranial magnetic stimulation ("TMS") or radiofrequency ("RF") ablation, can benefit from individualized maps of electrical properties, as would diagnostic techniques such as electro- or magneto-encephalography ("EEG" or "MEG"), which can be founded upon electromagnetic source localization.

Magnetic Resonance Imaging ("MRI") can provide noninvasive volumetric information about the interior magnetic environment of tissue or materials, and various attempts have been made to use this information to circumvent the ill-posed inverse problem of electrical prospection. In particular, MRI can be used to map the distribution of internal magnetic fields resulting from currents or fields applied to a body. This information can be used to deduce distributions of electrical properties in vivo. However, certain key information can be missing from magnetic resonance ("MR")-based measurements. For example, the absolute phase distribution of the RF magnetic field can generally be considered to be fundamentally inaccessible due to the nature of signal excitation and detection in magnetic resonance. The absolute distribution of RF signal sensitivity can be fundamentally entangled with the unknown distribution of magnetization in a body. It has been recognized that access to this absolute field-related information can facilitate calculation of useful quantities such as local energy deposition in MRI, in addition to the electrical property distribution. Recently, various ingenious approximations have been applied to derive or bypass absolute RF phase, generally involving symmetry assumptions about the body or the probe used to image it. These approximations, however, can break down precisely when fields can be most perturbed by tissue properties, (e.g., at high operating frequencies) when MR-based techniques should otherwise perform best, and when local energy deposition can be of most concern.

Thus, there may be a need for providing exemplary systems, methods and computer-accessible mediums for facilitating noninvasive mapping of electrical properties of tissue or materials, which addresses both the prior problems of noninvasive electrical property mapping, and the more recent and circumscribed problem of determination of absolute RF phase and magnetization distribution in MRI, and which can overcome at least some of the deficiencies described herein above.

SUMMARY OF EXEMPLARY EMBODIMENTS

According such needs can be addressed with the exemplary embodiments of system, method, and computer-accessible medium for facilitating noninvasive mapping of electrical properties of tissue or materials according to the present disclosure.

For example, exemplary systems, methods, and computer-accessible mediums can be provided for determining at least one property(ies) (e.g., an electrical property or a cross-section property) of a target(s). For example, it can be possible to determine electromagnetic-field-related quantities associated with signals provided from the target(s). The electromagnetic-field-related quantities can be provided to procedures to relate the electromagnetic-field-related quantities to a plurality of unknown electrical property values and residual field-related unknown values of the target(s).

In some exemplary embodiments of the present disclosure, the electromagnetic-field-related quantities can be determined from a transmit pattern(s) and a receive pattern(s). The plurality of unknown electrical property values and residual field-related unknown values can be determined from a unique solution to an expression(s) that can be derived from the transmit pattern(s) and the receive pattern(s). The expression(s) can include only transverse components. The transmit pattern(s) can be based on a spatial distribution of a magnetic field used for signal excitation, and the receive(s) pattern can be based on a distribution of signal sensitivity in receiving element(s).

In certain exemplary embodiments of the present the disclosure, non-transverse components can be eliminated using combinations of a plurality of expression(s). Non-transverse components can also be eliminated using a relation(s) governing a behavior of electromagnetic fields, which can include Gauss's law. The target(s) can include a material(s) that can have anisotropic electrical property tensors or that can have scalar properties with a non-vanishing electrical property gradient. The material(s) can include a tissue(s). The residual field-related unknown values can include a value(s) derived from an absolute phase of an electromagnetic field.

In another exemplary embodiment is an exemplary system, method, and computer-accessible medium for determining a property(s) of a target(s), including determining electromagnetic-field-related quantities associated with signals provided from the target(s), providing the electromagnetic-field-related quantities to procedures to relate the electromagnetic-field-related quantities to a plurality of unknown electrical property values and residual field-related unknown values of the target(s), and determining an electrical property(s) or the cross-sectional property(s) of the target(s) by determining the plurality of unknown electrical property values and residual field-related unknown values of the target(s). The property(s) can include an electrical property(s) or a cross-sectional property(s).

These and other objects, features and advantages of the exemplary embodiments of the present disclosure will become apparent upon reading the following detailed description of the exemplary embodiments of the present disclosure, when taken in conjunction with the appended claims.

BRIEF DESCRIPTION OF THE DRAWINGS

Further objects, features and advantages of the present disclosure will become apparent from the following detailed description taken in conjunction with the accompanying Figures showing illustrative embodiments of the present disclosure, in which:

FIGS. 5A-5C are exemplary conductivity maps according to an exemplary embodiment of the present disclosure;

FIGS. 6A-6C are exemplary permittivity maps according to an exemplary embodiment of the present disclosure;

Figure 1:
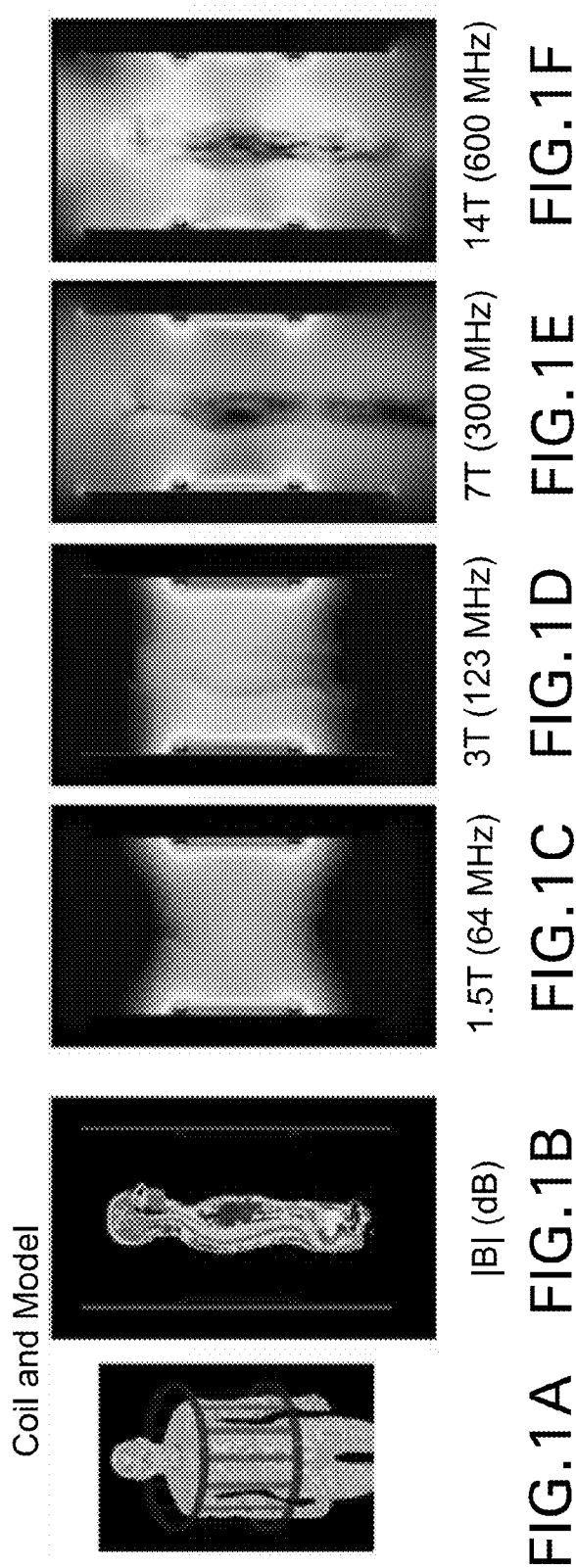
FIGS. 1A-1F are exemplary images illustrating magnetic fields shaped by electrical properties prior to the exemplary Local Maxwell Tomography.

Throughout the drawings, the same reference numerals and characters, unless otherwise stated, are used to denote like features, elements, components, or portions of the illustrated embodiments. Moreover, while the present disclosure will now be described in detail with reference to the figures, it is done so in connection with the illustrative embodiments and is not limited by the particular embodiments illustrated in the figures, or the accompanying claims.

DETAILED DESCRIPTION OF EXEMPLARY EMBODIMENTS

The exemplary embodiments relate to exemplary systems, methods, and computer-accessible mediums which can utilize a Local Maxwell Tomography ("LMT") approach, according to an exemplary embodiment of the present disclosure, and can facilitate a noninvasive mapping of electrical properties of tissue or materials. The utilized exemplary LMT technique can provide a new approach to noncontact mapping of electrical properties, based on cross-sectional magnetic resonance measurements of the perturbations of RF magnetic fields. This exemplary approach can determine high-frequency electrical property distributions without prior assumptions, determine the absolute phase of applied RF fields (once considered fundamentally inaccessible in magnetic resonance), and can be generalized to other material property measurements based on incomplete internal information.

Unlike prior field-based property mapping methods such as electrical properties tomography ("EPT"), which can be derived as a special case, the exemplary LMT approach can be free of assumptions regarding RF phase and coil/field/magnetization structure. One exemplary LMT approach, such as the one described in U.S. application Ser. No. 13/314,105, utilizes a non-invasive mapping, and can retain certain simplifying assumptions: (a) an assumption of scalar electrical properties, ignoring structural anisotropies which can be found in complex materials and (b) an assumption of piecewise constant or slowly varying properties, ignoring the effects of electrical property gradients upon local electrodynamics.

Exemplary embodiments of the exemplary system, method, and computer-accessible medium which utilize a generalized LMT framework described herein can improve the exemplary LMT approach discussed in U.S. application Ser. No. 13/314,105. Such exemplary improved LMT approach can remove the two assumptions discussed above by manipulating the LMT equations to exclude certain unknown terms. The exemplary embodiments of the LMT framework described herein can be generalized to encompass the electrodynamic effects of (a) non-vanishing spatial gradients of electrical properties, for example, at tissue boundaries, and (b) structural anisotropies resulting in non-trivial electrical property tensors, which can facilitates more accurate property maps and new applications in anisotropic materials, (e.g., biological tissues such as the brain). For example, the exemplary generalized LMT framework described herein can eliminate edge artifacts observed in simpler implementations and the tensor structures can also be determined if a sufficient number of measurements and coil elements can be deployed, which can facilitate electrical property tractography.

Thus, the exemplary system, method, and computer-accessible medium which utilize generalized LMT approach described herein, in which local gradients of coil-independent unknowns can be derived together with electrical property values, can be sufficiently general to accommodate spatial variations and anisotropies in conductivity and permittivity.

Exemplary Approaches Using Local Maxwell Tomography

The exemplary LMT framework can involve measuring the curvature of RF magnetic fields in the presence of a body—a phenomenon responsible for known imaging artifacts particularly at high operating frequency—and applying a local formulation of Maxwell's equations which can be solved simultaneously for local gradients of unknown phase and magnetization along with the unknown permittivity and conductivity. This exemplary LMT approach can utilize complementary tomographic information from multiple RF transmit and receives coils to determine uniquely the coil-independent phase-, magnetization-, and electrical-property-related unknowns. Use of the exemplary LMT procedure can, for example, eliminate the spatiotemporal coupling associated with Maxwell's differential equations, and can facilitate a unique solution, voxel-by-voxel via an overdetermined local system of equations. Such exemplary approach can facilitate quantitative determination of both conductivity and permittivity throughout the volume, based only on MR measurement, and free of symmetry assumptions or constraints on body/probe geometry. The exemplary LMT procedure can also facilitate a determination of local gradients of absolute magnetization (e.g., parameters which can be useful for quantitative imaging and which can otherwise only be approximated at high field strength) as well as for providing rich information about the distribution of previously unmeasurable components of RF magnetic and electric field within a body. The exemplary LMT approach, moreover, can represent an exemplary embodiment of a general class of procedures for an inverse problem solution: similar approaches can be applied for local determination of other material property distributions based on incomplete interior measurements of perturbations described generally by partial differential equations.

FIGS. 1A-1F illustrate exemplary images of magnetic fields perturbed by the spatially varying electrical properties of a body. LMT can exploit this spatial information, as measured in a set of RF coils, to derive cross-sectional maps of internal electrical properties. Various exemplary images illustrated in FIG. 1A-1F compare the simulated RF magnetic field, conventionally labeled B1, produced by an encircling birdcage body coil operating at a variety of frequencies, in the presence of a human body model with electrical properties manually assigned to segmented tissue types based on invasively-obtained values. As shown in FIGS. 1A-1F, the spatial distribution of the absolute value of the simulated RF magnetic field $|B_1|=(|B_{1,x}|^2+|B_{1,y}|^2+|B_{1,z}|^2)^{1/2}$ produced by an encircling birdcage body coil in the presence of a human body model (see. e.g., FIG. 1A) in an exemplary numerical simulation was displayed on a log scale for a variety of exemplary operating frequencies: 64 MHz (FIG. 1C), corresponding to the Larmor frequency of protons in a 1.5 Tesla ("T") MR scanner; 123 MHz, corresponding to 3 T operation (FIG. 1B); 300 MHz, corresponding to 7 T (FIG. 1E); and 600 MHz, corresponding to 14 T (FIG. 1F). The maximum RF field value corresponding to the 0 dB reference in the color map at right was $2\times10^{-5}$ T. Electrodynamic simulations were performed using the Finite Difference Time Domain ("FDTD") approach with the XFDTD 6.6 software suite (e.g., Remcom, State College, Pa., USA). The "Duke" human body model was employed, at 5×5×5 mm3 cell resolution, with permittivity and conductivity adjusted according to known frequency dependencies. A 16-rung high-pass birdcage coil model was used, and fields were collected in the steady state following application of a unit sinusoidal voltage.

Referring to FIG. 1C, at the lowest operating frequency shown (e.g., 64 MHz, corresponding to a 1.5 Tesla MR scanner), the field distribution appears nearly independent of detailed body structure, as can be expected in the quasistatic limit. However, as the operating frequency increases in the exemplary simulations, a ghostly image of the body appears to emerge. The appearance of distinct body structures within the field distribution at high operating frequency reflects the differential field curvature induced by the differing electrical properties of distinct tissues. Though the subject-specific inhomogeneity of field distributions at high frequency has in the past been considered a significant challenge for high-field MRI, this inhomogeneity can contain information regarding the spatial distribution of tissue electrical properties.

In order to extract the information, Maxwell's equations can be applied to derive convenient local expressions relating field curvature to electrical property values. The incomplete local field information obtained from a sufficient number of distinct MR transmitters and detectors can be inserted into the Maxwell's equation to solve for key spatial derivatives of the missing field-related quantities, in addition to the local electrical properties. The physical requirement or preference that electrical properties, and other local unknown quantities be consistent among all coils can result in unique solution via an overdetermined system of equations relating coil-dependent known values to the coil-independent unknowns.

Exemplary Electrodynamics

For a magnetic resonance experiment associated with the mapping of RF magnetic field distributions, the relevant spin dynamics can occur over many Larmor frequency cycles on a time scale much longer than that of electromagnetic field transients. Thus, defining steady-state time-harmonically driven electric and magnetic fields of the form $E(r,t)=E(r)\exp(-i\omega t)$ and $B(r,t)=B(r)\exp(-i\omega t)$, where $\omega$ can be the angular frequency of the drive matching the Larmor frequency of spins of interest and r can represent spatial coordinates in the laboratory frame, and applying the Ohmic relation $J=\bar{\sigma}E$ and the constitutive relation $D=\bar{\epsilon}E$ for linear materials to the differential form of Ampère's Law, taking the curl, and substituting Faraday's Law, can yield the following exemplary equation relating electrical properties to the curvature of magnetic fields:

$$\nabla\times[(\bar{\sigma}-i\omega\bar{\epsilon})^{-1}\cdot(\nabla\times\bar{\mu}^{-1}B)]-i\omega B=0 \qquad (1)$$

For example, $\bar{\sigma}$, $\bar{\epsilon}$, and $\bar{\mu}$ can be 3×3 matrix representations of electrical conductivity, electric permittivity, and magnetic permeability tensors, respectively. The expressions $(\bar{\sigma}-i\omega\bar{\epsilon})^{-1}$ and $\bar{\mu}^{-1}$ in Eq. (1) can indicate matrix inverses. For the special case in which $\sigma$, $\epsilon$, and $\mu$ can be represented as scalar functions of position, Eq. (1) can be reduce to a generalized form of the Helmholtz equation:

$$(\nabla^2+k^2)B+F\times\nabla\times B+(\nabla-F)\times(U\times B)=0 \qquad (2)$$

where the following can be defined, for example:

$$k^2 \equiv i\omega\mu(\sigma-i\omega\in)$$

$$F \equiv \nabla \ln\{\mu(\sigma-i\omega\in)\} = \nabla \ln k^2$$

$$U \equiv \nabla \ln \mu \qquad (3)$$

Even with known electrical properties, Eqs. (1) or (2) can be insufficient to specify the precise functional form of electromagnetic fields in the absence of information on boundary conditions, which can include the geometry and time course of driving currents. However, if sufficient information can be available about the internal structure of the fields, the electrical properties can be deduced even in the absence of boundary condition information.

Exemplary Measurables and Inverse Problem

Substantial but ultimately incomplete information on internal field structure can be obtained from MR measurements. For example, true transverse RF magnetic field components can be expressed as products of measurables with unknown quantities as follows:

$$B_{1,l}^{(+)} = \underbrace{(|B_{1,l}^{(+)}|\exp(i(\varphi_{B_{1,l}^{(+)}}+\varphi_{B_1^{(-)}})))}_{known}\underbrace{(\exp(-i\varphi_{B_{1,l_0}^{(-)}}))}_{unknown} \equiv \qquad (4)$$

$$\underbrace{(|B_{1,l}^{(+)}|\exp(i\varphi_{\Sigma_l}))}_{know}\underbrace{(\exp(-i\varphi_0))}_{unknown}$$

$$B_{1,l'}^{(-)} = \underbrace{(|MG_{l'}B_{1,l'}^{(-)}|\exp(i(\varphi_{B_{1,l'}^{(-)}}-\varphi_{B_{1,l_0}^{(-)}})))}_{known}\underbrace{\left(\frac{1}{|MG_{l'}|}\exp(+i\varphi_{B_{1,l_0}^{(-)}})\right)}_{unknown} \equiv \qquad (5)$$

$$\underbrace{(|MG_{l'}B_{1,l'}^{(-)}|\exp(i\varphi_{\Delta_{l'}}))}_{known}\underbrace{\left(\frac{1}{|MG_{l'}|}\exp(+i\varphi_0)\right)}_{unknown}$$

In order to provide an exemplary solution to the LMT inverse problem, it can be possible to, for example, separate the right- and left-circularly polarized magnetic field components $B_1^{(\pm)}$ associated with each transmit coil 1 and each receive coil l' into known and coil-independent unknown quantities. The right- and left-circularly polarized field components $B_l^{(\pm)} \equiv B_{1x} \pm iB_{1y}$ can be used since these can be known to represent the distribution of MR transmit and receive sensitivities, respectively. Indices l and l' can indicate transmit and receive coils, respectively. The amplitude $|B_{1,l}^{(+)}|$, which can represent the distribution of spin excitations or nutation angles which can result from a unit current applied to transmit coil 1, can be determined quantitatively using any of a number of well-known "B1 mapping" techniques. The phases $\phi_{B_{1j}^{(+)}}$ and $\phi_{B_{1j}^{(-)}}$ can define the distribution of spin nutation axes for the transmit coil 1, or the reference phase distribution of the receive coil l', respectively. The function M can include all sources of signal variation that can be common to all coils and that may not be associated with electrodynamics. This can include the spatial distribution of equilibrium magnetization, as well as all non-electrodynamic phase variation $\phi_M$, for example, due to $B_0$ inhomogeneity, gradient eddy currents, incomplete RF spoiling, etc., which can be calibrated out via subtraction of appropriate reference phases. $G_r$ can be the spatially invariant overall gain of each receiver channel l', (e.g., the practical scaling factor), including an overall amplitude and phase which can be determined by intervening electronics, between underlying signal and measured voltage in each channel. Such exemplary quantities have been defined in Eqs. (4) and (5) with respect to the unknown phase distribution $\phi_0$ of a common reference receive coil or coil combination $l_0$.

Since the advent of magnetic resonance, this underlying absolute reference phase distribution has been viewed as fundamentally inaccessible. The measurable MR signal can result from a combination of RF excitation and reception processes, and the signal strength as a function of position can likewise be represented by a product of functions of the transmit sensitivity and the receive sensitivity. MR signal phase, therefore, can be a sum of transmit and receive phases, $$\varphi_{\Sigma_l} \equiv \varphi_{B_{1,l}^{(+)}} + \varphi_{B_{1,l_0}^{(-)}},$$

and, due to the handedness of spin precession, and the basic mechanisms of signal induction, these two phase contributions may not be equally distributed, particularly at high operating frequency. Relative transmit phases or relative receive phases such as $$\varphi_{\Delta_{l'}} \equiv \varphi_{B_{1,l'}^{(-)}} - \varphi_{B_{1,l_0}^{(-)}}$$

can be determined by taking quotients of appropriate signals.

A majority of MR applications can utilize only relative phase information, and the absolute reference phase remains an irrelevant quantity, like the spatially varying starting time of a set of local clocks. For the desired application of electrical property mapping described herein, however, absolute phase can matter: Maxwell's equations generally need consistent phase definitions at all points, and a spatially varying background phase can result in anomalous gradient terms if measured transmit or receive fields can be inserted into expressions like Eqs. (1) or (2). Moreover, apart from various approximations of convenience at low operating frequency, the absolute receive sensitivity distribution $|B_{1,l'}^{(-)}|$ may not be separated experimentally from the underlying distribution of magnetization |M| in the absence of prior information. The presence of a common non-electrodynamic background amplitude variation can also produce anomalous terms in Eqs. (1) or (2). Local Maxwell Tomography can provide a way to determine the absolute spatial variation of both amplitude and phase in MR, in addition to enabling quantitative mapping of electromagnetic fields and electrical properties.

The local inverse problem of the exemplary LMT approach can be formulated by, for example, inserting the field definitions in Eqs. (4) and (5) into the electrodynamic Eqs. (1) or (2), applying the product rule of differentiation, separating terms involving measured quantities from those involving unknowns, and collecting appropriate real and imaginary parts. Detailed exemplary derivations are described in more detail below. Thus, a set of master equations can be derived in which the unknown quantities can be the local values of $\sigma$ and $\in$, and a small number of low-order local derivatives of $\phi_0$ and |M|.

In regions of piecewise constant, electrical properties can be known a priori to lie at a distance from boundaries, the master equations can be linear in ten real quantities $\{\sigma, \epsilon, \nabla^2\phi_0, \nabla \ln |M|, \nabla^2 \ln |M|\}$. Each gradient operator $\nabla$ can be associated with three unknown vector components, for example, representing derivatives in the cardinal Cartesian directions, and $\nabla^2$ can be the scalar Laplacian operator. Thus, for slowly varying electrical properties (e.g., F=0), uncoupled Helmholtz equations can be written for each of the field components $B_1^{(\pm)}$, which, following application of the product law of differentiation, can result in linear matrix equations that can be solved for the unknowns $\{\sigma, \epsilon, \nabla\phi_0, \nabla^2\phi_0, \nabla \ln |M|, \nabla^2 \ln |M|\}$ at each spatial location.

Exemplary Generalized LMT Approach

The exemplary embodiments of the system, method, and computer-accessible medium which can utilize the generalized LMT approach according to the present disclosure described herein can facilitate accurate mapping that can occur in more general cases, for example, in boundary regions or in materials with anisotropic electrical property tensors. In these more general cases, non-vanishing electrical property gradients (e.g., F≠0) and/or anisotropies in property tensors can result in mixing of transverse and longitudinal RF field components. Physically, this mixing can correspond to field perturbations which can be linked to eddy currents and charge accumulations in the vicinity of interfaces or anisotropic structures. Thus, the exemplary embodiment of the generalized LMT approach, can manipulate the equations to remove terms involving the unknown coil-dependent longitudinal field component $B_{1z}$.

The manipulation of the equations can utilize applications of an additional gradient and use of Gauss' Law $\nabla \cdot B = 0$ to derive expressions involving only transverse components. The result can be a system of nonlinear master equations with an expanded set of local unknowns including up to third order derivatives. The uniqueness of solutions to these master equations can be a direct result of the inclusion of both transmit and receive measurements in the problem. The conjugate relationship of transmit and receive field phase to the common reference phase, for example, the opposite signs of the $\phi_0$ exponents in Eqs. (4) and (5), respectively, can break symmetry and facilitate variations in background phase to be distinguished from other electrical-property-related field variations. A detailed accounting of the number of equations and unknowns in the LMT inverse problem is described below. Generally, a set of two transmit-receive coils can suffice for solutions far from known property boundaries, eight transmit-receive coils suffices in principle to capture electrical property variations, and larger numbers of RF coil elements can result in improved robustness via increased degrees of overdetermination.

In such exemplary case, expanding the $F \times \nabla \times B$ term in Eq. (1) and defining can yield the following exemplary vector equation: $F_\pm \equiv (F_x \pm iF_y)/2$ can yield the following exemplary vector equation:

$$(\nabla^2 - F \cdot \nabla + k^2)B + F_- \nabla B_1^{(+)} + F_+ \nabla B_1^{(-)} + F_z \nabla B_z = 0 \quad (S6)$$

This equation can differ from the Helmholtz equation (S10). For example, the Helmholtz equation (S10) can be derived in piecewise constant scalar properties which is described below, and in the appearance of first derivative terms that supplement the Laplacian term and that, can mix transverse and longitudinal field components. Transverse field components $B_1^{(+)}$ and $B_1^{(-)}$ can be expressible in terms of measured quantities and coil-independent unknowns as in Eqs. (4) and (5), and the combination of $B_1^{(+)}$ and $B_1^{(-)}$ has been shown to be used in fixing the unknown phase $\phi_0$ for a local solution. Thus, the challenge in generalizing LMT can lie in removing terms involving the unknown coil-dependent longitudinal field component $B_{1z}$. In order to accomplish this task, it can be possible to divide Eq. (S6) by $F_z$, then either take the curl, or applying a z gradient, and using Gauss' Law $\nabla \cdot B = 0$ to derive expressions involving only transverse components:

$$\{(\nabla - \nabla \ln F_z) \times [(\nabla^2 - F \cdot \nabla + k^2)B + F_- \nabla B_1^{(+)} + F_+ \nabla B_1^{(-)}]\}_z = 0$$

$$(\nabla_z - \nabla_z \ln F_z)[(\nabla^2 - F \cdot \nabla + k^2)B_\pm + F_\mp \nabla_\pm B_1^{(+)} + F_+ \nabla B_1^{(-)}] - F_z \nabla_\pm (\nabla_- B_1^{(+)} + \nabla_+ B_1^{(-)}) = 0 \quad (S7)$$

In other exemplary embodiments the systems, methods, and computer-accessible mediums which utilize the exemplary generalized LMT approach, can be applied to other materials, such as tissue, nerve endings, and the like, and the exemplary generalized LMT approach is not limited to an element having electrical properties. Further, the exemplary technique of manipulating equations to remove the terms involving unknown variables is not limited to procedures involving MRI, and such technique can be used in other applications, for example, to determine cross-sectional mapping.

Exemplary Strategy for Solution of the Inverse Problem Using the Exemplary Generalized LMT Approach An exemplary strategy using the exemplary generalized LMT approach for solving more general cases of scalar properties with non-vanishing local gradients, for example, cases in which F≠0 and local gradients in electrical properties can be allowed, is discussed below. In this exemplary general case, it can be assumed that U=0, and, that variations in magnetic permeability can be sufficiently small such that a homogeneous scalar value can be defined, which can generally be the case for typical biological tissues, and a variety of other common materials.

where the following can be defined as, for example:

$$\nabla_z \equiv \partial/\partial z, \nabla_\pm \equiv \partial/\partial x \pm i\partial/\partial y$$

For each of the three relations in Eq. (S7), terms associated with $B_1^{(+)}$ and $B_1^{(-)}$, respectively, can be grouped in the following exemplary general format:

$$O_- B_1^{(+)} + O_+ B_1^{(-)} = 0 \quad (S8)$$

where $O_\pm$ operators can contain derivatives of various orders and coil-independent coefficients involving field-related quantities and electrical properties.

To eliminate references to unknown absolute field amplitudes and phases, it can be possible to take the ratios of expressions for distinct coils and arrive at the following general master equations:

$$\frac{B_{1l}^{(+)}}{B_{1m}^{(+)}}\left\{\frac{O_- B_{1l}^{(+)}}{B_{1l}^{(+)}}\right\}\left\{\frac{O_+ B_{1m'}^{(-)}}{B_{1m'}^{(-)}}\right\} - \frac{B_{1l}^{(-)}}{B_{1m'}^{(-)}}\left\{\frac{O_+ B_{1l'}^{(-)}}{B_{1l'}^{(-)}}\right\}\left\{\frac{O_- B_{1m}^{(+)}}{B_{1m}^{(+)}}\right\} = 0 \quad (S9)$$

Each of the expressions in brackets can be written as for Eq. (S10) in terms of derivatives of logarithms, and a nonlinear optimization procedure of choice can be used for an exemplary solution. If all the useful components of Eq. (S7) can be used, there can be, for example, 46 real unknowns and six real equations per transmit-receive coil pair, and thus a unique solution can utilize at least eight transceiver coils. Unlike in regions of piecewise constant (e.g., F=0), which is further described below, both $B_1^{(+)}$ and $B_1^{(-)}$ and can be needed for each coil.

In some exemplary embodiments, subsets of the component equations with fewer unknowns, but also with fewer equations and a reduced degree of over-determination, can be used.

With the addition of still larger numbers of unknowns, a similar exemplary approach to eliminating unmeasured field components $B_{1,z}$, with appropriate derivatives and applications of Gauss' Law, can also be used to solve the fully general Eq. (1) for electrical property tensors.

In addition, an entirely local formulation in which an independent solution can be derived for each voxel, each derivative order of unknown quantities can be represented by an independent unknown. However, more global formulations can also be possible in which property values and other unknowns can be determined at multiple connected voxels, thereby defining associated derivatives. Such exemplary approaches, which can also incorporate additional anatomical or physical constraints, can have higher degrees of over-determination than fully local formulations, but at the price of substantially larger search spaces.

Exemplary Results Using the Exemplary Generalized LMT Approach

Figure 2:
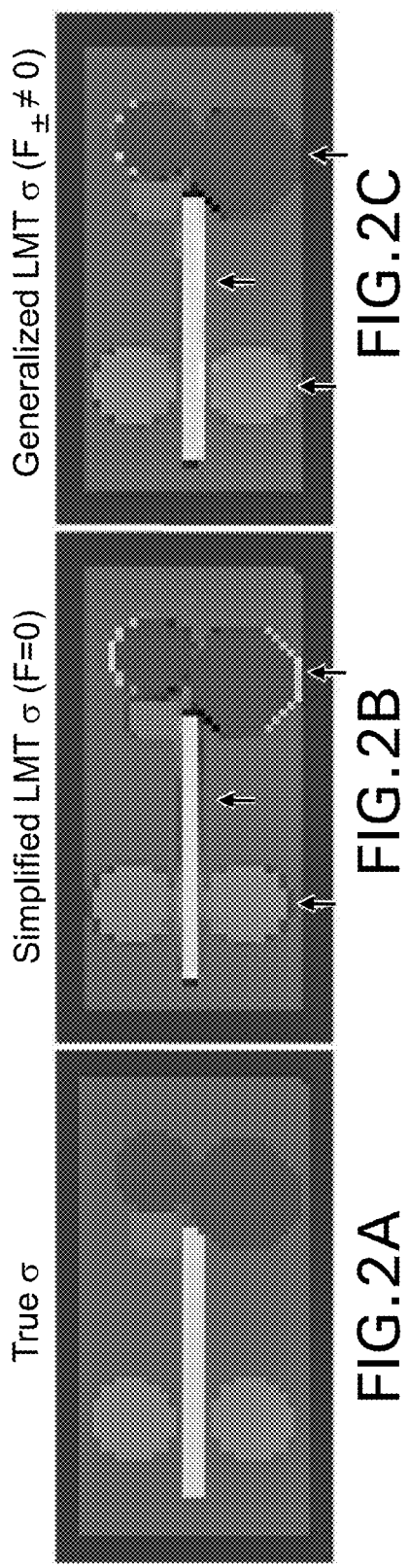
FIGS. 2A-2C are exemplary conductivity maps according to an exemplary embodiment of the present disclosure.

FIGS. 2A-2C are exemplary images illustrating exemplary results produced using the exemplary systems, methods, and computer-accessible mediums which utilize the exemplary LMT approach described herein. For example, the illustrations provided in FIGS. 2A-2C indicate a comparison of conductivity maps at 7 Tesla field strength in a simplified cylindrical body model with heart, lung, spinal cord, kidney, and muscle compartments, using a simulated 16-element array geometry with 4×2 grids of rectangular elements placed on the anterior and posterior surfaces of the body. Finite difference time domain software ("XFDTD", Remcom, College Station, Pa.) was used to compute the magnetic fields produced in the simplified body model after steady-state excitation of each of the sixteen array elements with a unit-amplitude sinusoidally-varying voltage at the 7 T Larmor frequency of 300 MHz. The model was constructed to mimic some aspects of the human torso, with spherical "kidneys," "lungs," and "heart" each assigned the tabulated electrical property values for the corresponding human tissue at about 300 MHz, and a narrow cylindrical spinal column with the electrical properties of cerebrospinal fluid, all embedded in a cylinder with skeletal muscle properties. The measurable quantities identified in Eqs. (4) and (5) (e.g., $\{|B_{1,t}^{(+)}|\cdot\phi_{\Sigma_t}, |MB_{1,t'}^{(-)}|\cdot\phi_{A_{t'}}\}$) were derived using a phased combination of all sixteen coils to define the reference phase $\phi_0$ which was subsequently discarded, and these quantities were used as inputs for the exemplary LMT reconstruction. LMT property maps using the F=0 approximation were compared with generalized LMT property maps assuming only Fz=0. As indicated by arrows 205, a generalized LMT reconstruction (see e.g., FIG. 2C) can remove many of the artifactual stripes at property boundaries seen in a simplified reconstruction incorrectly assuming that F=0 (see e.g., FIG. 2B). For ease of implementation, the exemplary procedure employed to generate the illustrative results assumed vanishing longitudinal property gradients, yielding notable residual errors in the z direction (e.g., left-right).

Figure 3:
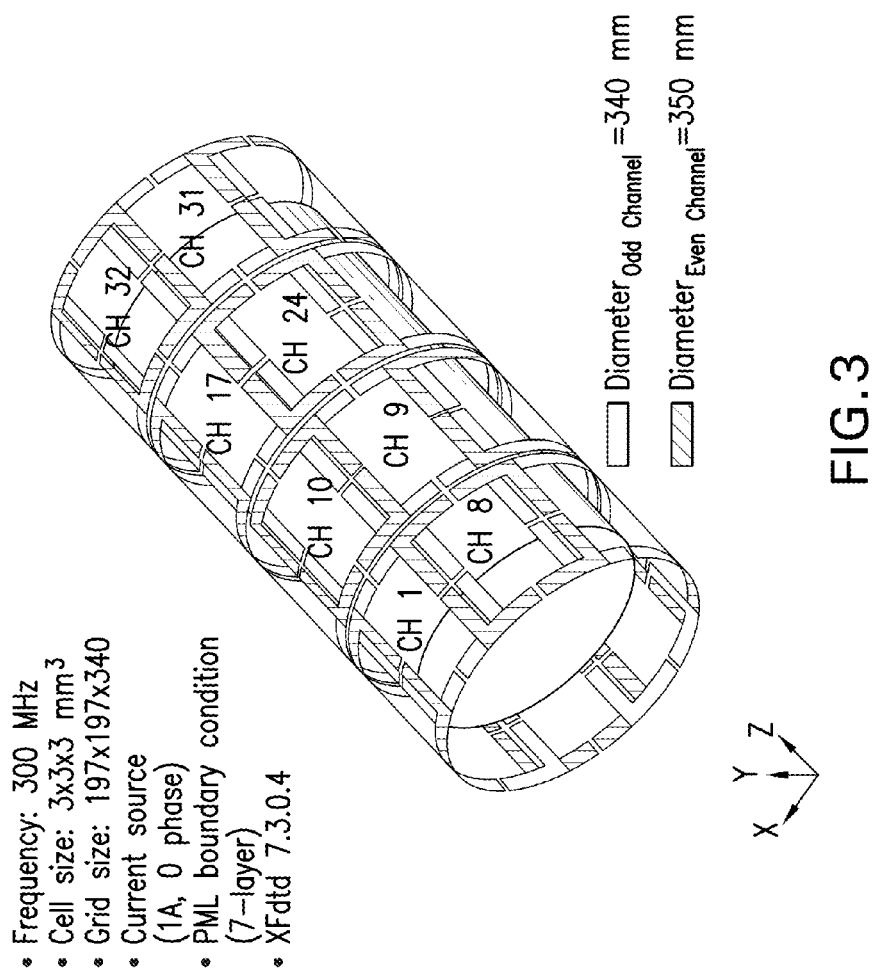
FIG. 3 is an exemplary illustration of an exemplary simulated coil array according to an exemplary embodiment of the present disclosure.
Figure 4:
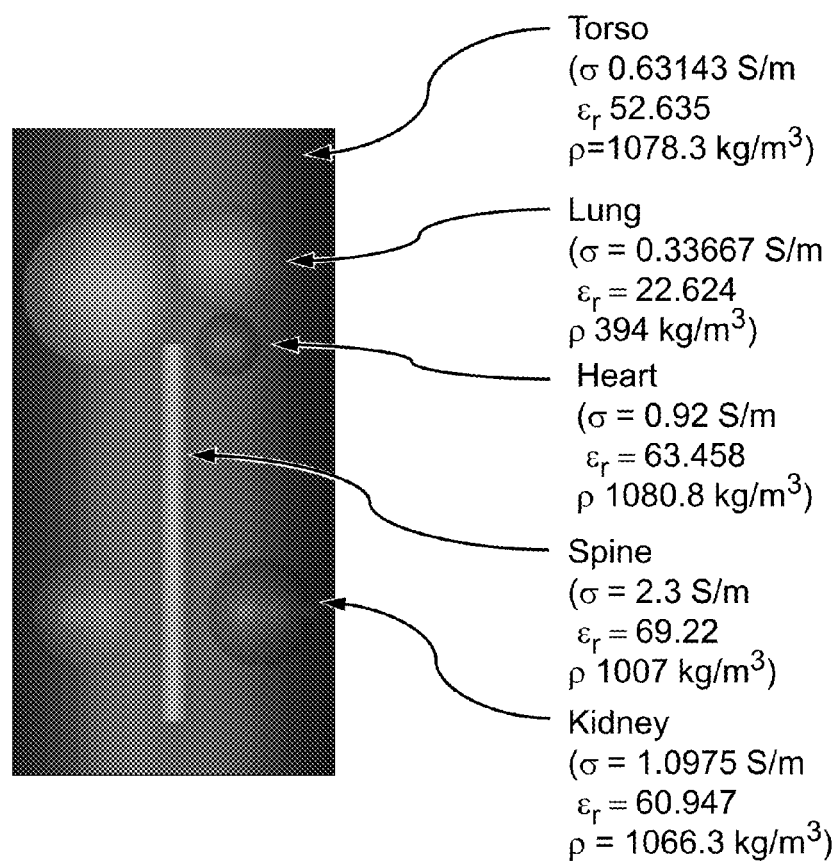
FIG. 4 is an exemplary illustration of an exemplary body model according to an exemplary embodiment of the present disclosure.

FIG. 3 shows an exemplary illustration of an exemplary simulated coil array used to generate additional exemplary results. The exemplary simulated coil array included a 32-element encircling coil used for validation of the exemplary generalized LMT in FDTD simulations (using the XFDTD 7.3.0.4 software by Remcom, Inc.), including a frequency of 300 MHz, a cell size of 3×3×3 mm³, a grid size of 197×197×340, a current source of 1 amp with a phase of 0, and perfectly matched layer ("PML") boundary conditions of 7 layers. Additionally, the diameter of the odd-numbered array elements was about 340 mm and the diameter of the even-numbered array elements was about 350 mm. FIG. 4 is an exemplary diagram of an exemplary body model used in the exemplary simulations. The exemplary body model had electrical properties associated with different tissue types assigned to internal structures, as shown in FIG. 4.

FIGS. 5A-5C show exemplary conductivity maps of the exemplary LMT. The exemplary simulations (e.g., using the exemplary models shown in FIGS. 3 and 4), illustrate that the exemplary LMT can yield substantially correct values of electrical properties throughout the body. For example, FIG. 5A illustrates an F=0 approximation maps, not accounting for perturbed electrodynamics at electrical property boundaries; residual errors can be seen at property boundaries. FIG. 5B illustrates the exemplary generalized LMT maps, assuming only Fz=0, accounting for the full electrodynamics at all boundaries except z-directed boundaries; the elimination of residual edge artifacts at all boundaries with no z component can be seen. Additionally, the Fz=0 assumption was used only for computational convenience, and this assumption can be removed. FIG. 5C shows true conductivity maps (e.g., maps of the parameters used as inputs into the FDTD simulation) for comparison.

FIGS. 6A-6C shows exemplary permittivity maps of the exemplary LMT. The exemplary simulations illustrate that the exemplary LMT can yield substantially correct values of electrical properties throughout the body. FIG. 6A illustrates an F=0 approximation maps, not accounting for perturbed electrodynamics at electrical property boundaries; residual errors can be seen at property boundaries. FIG. 6B illustrates the exemplary generalized LMT maps, assuming only Fz=0, accounting for the full electrodynamics at all boundaries except z-directed boundaries; the elimination of residual edge artifacts can be seen at all boundaries with no z component. Additionally, the Fz=0 assumption was used only for computational convenience, and this assumption can be removed. FIG. 6C illustrates true relative permittivity maps (i.e. maps of the parameters used as inputs into the FDTD simulation) for comparison.

Figures 7A, 7B, 7C:
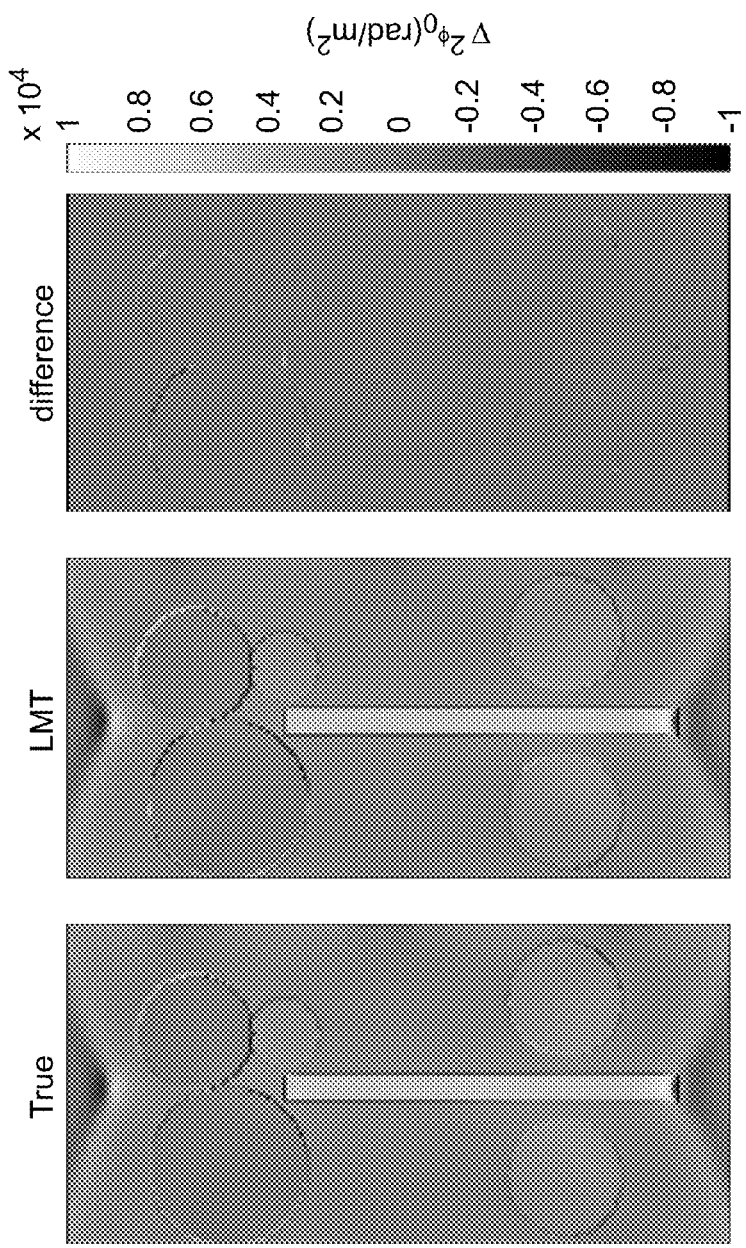
FIG. 7A-7C are exemplary $\nabla^2 \phi_0$ maps according to an exemplary embodiment of the present disclosure.

FIGS. 7A-7C show exemplary $\nabla^2\phi_0$ maps of the exemplary LMT. A missing phase can be recovered via the exemplary generalized LMT. The exemplary simulations provided therein illustrate that, in addition to facilitating the mapping of electrical properties throughout the body, the exemplary LMT can also yield substantially correct values of the Laplacian of the missing RF phase reference $\phi_0$. FIG. 7A illustrates a true distribution of the Laplacian of the missing phase. FIG. 7B illustrates a distribution map of the Laplacian of the missing phase recovered using the exemplary generalized LMT with the Fz=0 approximation used for convenience only. FIG. 7C shows an illustration of the difference between the true and exemplary LMT-generated maps. The exemplary LMT-based maps can be correct even at boundaries (with the exception of z-directed boundaries in the case of the Fz=0 approximation used here—an approximation which may be eliminated as needed).

Figure 8:
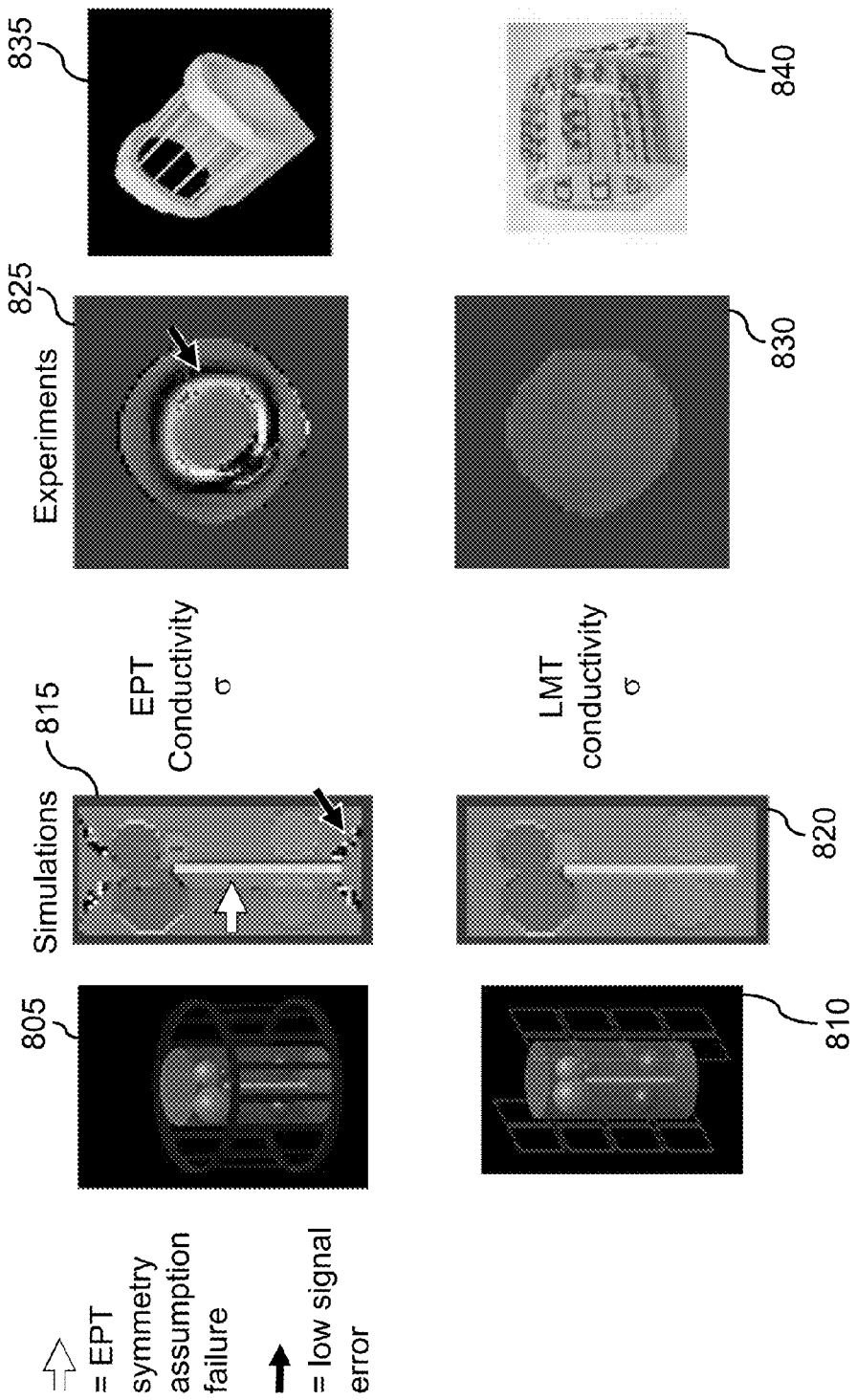
FIG. 8 is a set of illustration providing Local Maxwell Tomography with F=0 compared to Electrical Properties Tomography.

FIG. 8 shows a set of illustration of LMT with F=0 compared to previously-known techniques. Here, the exemplary LMT used an F=0 approximation. These exemplary comparisons demonstrate, e.g., in simulations and experimental implementations in an imaging phantom, the advantages of the exemplary LMT, even with the F=0 approximation, as compared with previously-known techniques such as Electrical Properties Tomography ("EPT"). EPT, as performed with a birdcage coil (elements 805 and 835) at 7 T, resulted in notable errors in conductivity maps (e.g., elements 815 and 825) in regions of low coil sensitivity, as well as errors associated with additional symmetry assumptions required by EPT. The exemplary LMT procedure, using multi-element coil arrays (e.g., elements 810 and 840), here removed these errors completely, as can be seen in the resulting LMT conductivity maps (e.g., elements 820 and 830). In the LMT simulation, the only errors remaining were those associated with the F=0 approximation, which can be removed using generalized LMT.

Figure 9:
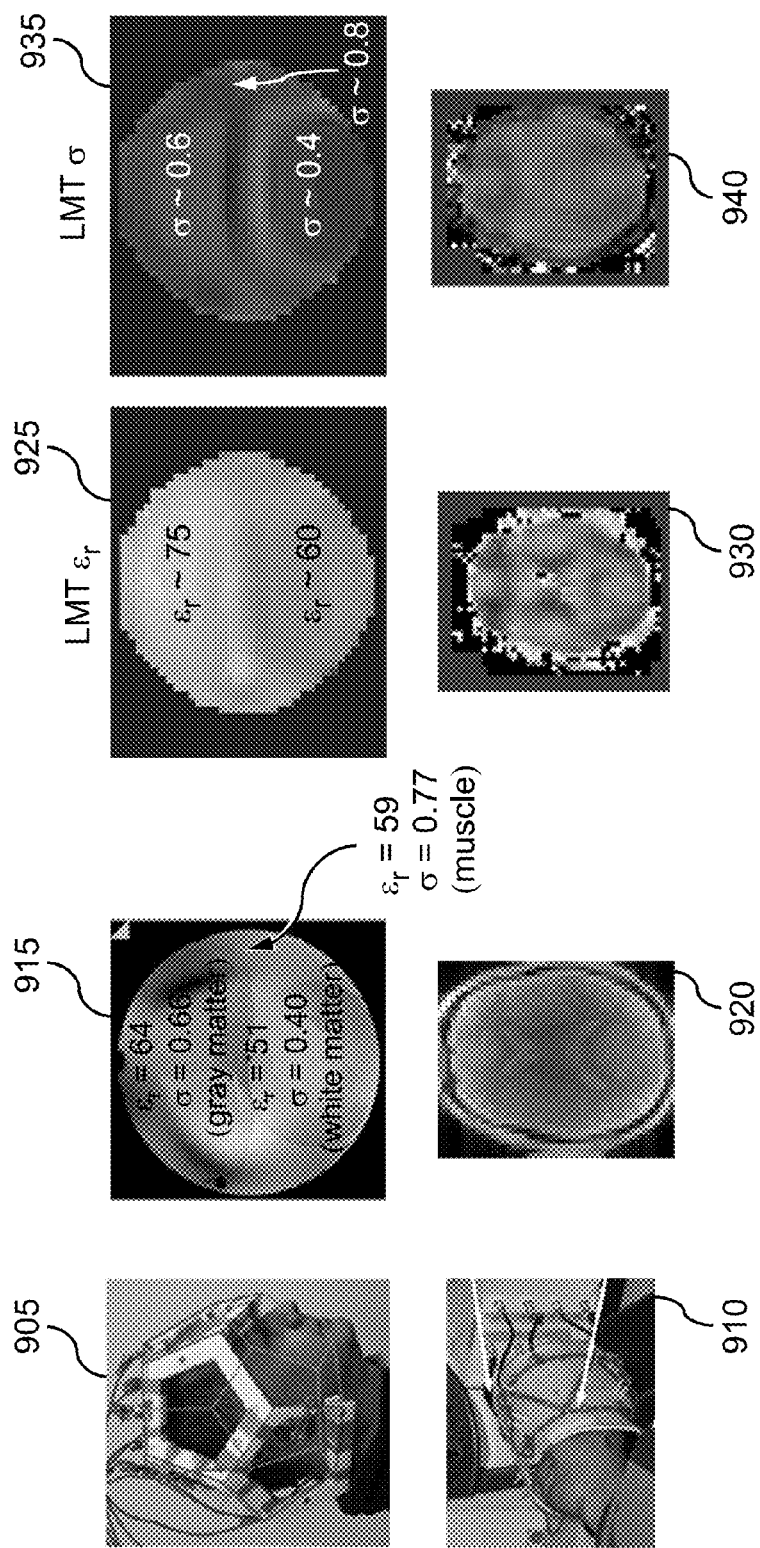
FIG. 9 is a set of images illustrating phantom and in-vivo experiments using the exemplary Local Maxwell Tomography with F=0 according to an exemplary embodiment of the present disclosure.

FIG. 9 shows a set of exemplary illustrations of phantom and ii-vivo experiments using the exemplary LMT with an F=0 approximation. Validations were performed at 7 T field strength using the exemplary coil shown (e.g., element 905) surrounding an imaging phantom divided into multiple compartments with different electrical properties. Electrical properties measured in-situ by invasive probes are superimposed on the phantom image of the coil (e.g., element 915). The exemplary LMT correctly identified the differences in electrical properties noninvasively (e.g., elements 925 and 935). Validations were also performed at 7 T field strength using the exemplary coil (e.g., element 910) and a healthy adult volunteer (e.g., element 910). The exemplary LMT-derived permittivity (e.g., element 930) and conductivity (e.g., element 940) maps show structure consistent with known brain anatomy. For comparison, a cross-sectional MR image of the volunteer's brain is shown (e.g., element 920).

Exemplary Performances of LMT

The exemplary systems, methods, and computer-accessible mediums which utilize the exemplary LMT approach/technique, can derive local values of missing properties, phases, and amplitudes, without need for a solution of differential equations, and without reference to boundary conditions. Once electrical properties can be known throughout a volume of interest, it can be possible to return to, and/or utilize, traditional differential equation methods, using an appropriate coil model, and solve for quantities of interest such as the longitudinal RF magnetic field $B_{1z}$, the RF electric field E, and the local energy deposition σE·E. Direct recovery of all components of B and E can also be formulated locally in a model-free manner using the exemplary LMT approach, but for some additional calibration of the absolute scaling of $B_1^{(-)}$ with respect to $B_1^{(+)}$ can be needed.

Thus, for example, the exemplary systems, methods and computer-accessible mediums, which utilize the LMT approach, can use measurements of RF magnetic field perturbations by electrical properties of a body—perturbations often considered an Achilles heel of high-field MRI—to map those properties along with gradients of key field-related quantities. Use of local gradients as unknowns can be a robust approach for local solution of Maxwell's equations with incomplete interior measurements. Rather than attempting a global solution, for example, with Green's functions or finite difference/finite element numerical approaches, the exemplary systems, methods, and computer-accessible mediums, which utilize the exemplary LMT approach, can use local measurements to constrain the problem to a small list of probe-independent local unknowns. Prior approximate approaches can be derived directly as special cases of the general LMT formalism, for example, by applying relevant symmetry assumptions.

Various other special cases with practical advantages of speed or simplicity can also be derived from the exemplary LMT formalism. Further, exemplary procedures which can be similar to the exemplary LMT method/approach/procedure can be applied in for a variety of other cases in which material properties can be determined by, for example, producing perturbations and observing responses dictated by partial differential equations. For example, the exemplary LMT method/approach/procedure can be applied to noncontact spatial mapping of thermal properties.

With the exemplary LMT approach/procedure, it can be possible to measure properties at a Larmor frequency of interest, generally high MHz for substantial tissue-field interactions. For example, at 7 T, a robust measurement of local field derivatives can be achieved, although this is also feasible at lower field strengths. Meanwhile, a formulation of the exemplary LMT procedure/approach for longitudinal fields only can, for example, facilitate low-frequency electrical property mapping as well.

Figure 10:
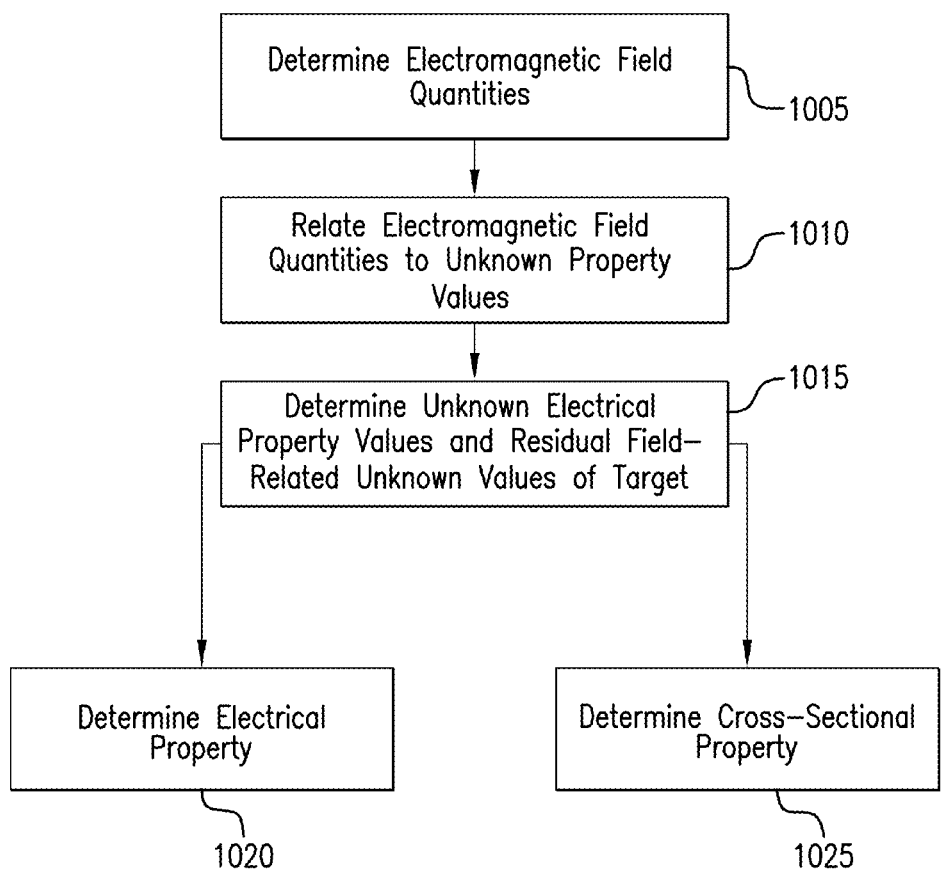
FIG. 10 is a flow diagram illustrating a method for determining an electrical property or a partial cross-sectional property according to an exemplary embodiment of the present disclosure.

FIG. 10 is a flow diagram illustrating a method for determining an electrical property or a partial cross-sectional property of a target according to an exemplary embodiment of the present disclosure. At procedure 1005, electromagnetic field quantities can be determined. At procedure 1010, the electromagnetic field quantities can be related to unknown property values. At procedure 1015, unknown electrical property values and residual field-related unknown values of the target can be determined. At procedure 1020, the electrical property of a target can be determined. Alternatively, or in addition, at procedure 1025, a cross-sectional property of the target can be determined.

Exemplary Strategies for Solution of the Inverse Problem in Piecewise Constant Scalar Properties (F=0)

For purposes of illustration only and not to limit the present disclosure, an exemplary strategy for solving the inverse problem in a case of F=0 and U=0, for example, piecewise constant scalar properties, for example, in homogeneous tissue regions at a distance from boundaries, is described as follows. For example, in such cases, Eq. (2) can reduce to a true Helmholtz equation, which can be expanded as follows:

$$\frac{\nabla^2 B_1^{(\pm)}}{B_1^{(\pm)}} + k^2 = \nabla^2 \ln B_1^{(\pm)} + \nabla \ln B_1^{(\pm)} \cdot \nabla \ln B_1^{(\pm)} + \omega^2 \mu \varepsilon + i\omega\mu\sigma \approx 0 \tag{S10}$$

Plugging expressions for $B_1^{(\pm)}$ from Eq.'s (4) and (5) into Eq. (S10), grouping all known quantities and unknown quantities, and rewriting in matrix form, provides for example:

$$\overbrace{\begin{bmatrix} A_{11}^{(l)} & A_{12}^{(l)} & A_{13}^{(l)} & -1 & 0 & 0 & 0 & 0 & 0 & 0 & 1 & 0 \\ A_{21}^{(l)} & A_{22}^{(l)} & A_{23}^{(l)} & 0 & -1 & 0 & 0 & 0 & 0 & 0 & 0 & 1 \\ A_{31}^{(l')} & A_{32}^{(l')} & A_{33}^{(l')} & -1 & 0 & A_{41}^{(l')} & A_{42}^{(l')} & A_{43}^{(l')} & 1 & -1 & 0 & 1 & 0 \\ A_{41}^{(l')} & A_{42}^{(l')} & A_{43}^{(l')} & 0 & 1 & A_{31}^{(l')} & A_{32}^{(l')} & A_{33}^{(l')} & 0 & 0 & -1 & 0 & 1 \end{bmatrix}}^{A} \overbrace{\begin{bmatrix} \partial\varphi_0/\partial x \\ \partial\varphi_0/\partial y \\ \partial\varphi_0/\partial z \\ \nabla\varphi_0 \cdot \nabla\varphi_0 \\ \nabla^2\varphi_0 \\ \partial\ln|M|/\partial x \\ \partial\ln|M|/\partial y \\ \partial\ln|M|/\partial z \\ \nabla\ln|M| \cdot \nabla\ln|M| \\ \nabla^2\ln|M| \\ 2\nabla\varphi_0 \cdot \nabla\ln|M| \\ \omega^2\mu\varepsilon \\ \omega\mu\sigma \end{bmatrix}}^{x} = \overbrace{\begin{bmatrix} b_1^{(l)} \\ b_2^{(l)} \\ b_3^{(l')} \\ b_4^{(l')} \end{bmatrix}}^{b} \tag{S11}$$

The following matrix and vector element definitions apply to Eq. (S11):

$$A_{11}^{(l)} = 2\partial\varphi_{\Sigma_l}/\partial x \qquad A_{12}^{(l)} = 2\partial\varphi_{\Sigma_l}/\partial y \qquad \text{(S12)}$$

$$A_{13}^{(l)} = 2\partial\varphi_{\Sigma_l}/\partial z$$

$$A_{21}^{(l)} = -2\partial\ln|B_{1,l}^{(+)}|/\partial x \quad A_{22}^{(l)} = -2\partial\ln|B_{1,l}^{(+)}|/\partial y$$

$$A_{23}^{(l)} = -2\partial\ln|B_{1,l}^{(+)}|/\partial z$$

$$A_{31}^{(l')} = -2\partial\varphi_{\Delta_{l'}}/\partial x \quad A_{32}^{(l')} = -2\partial\varphi_{\Delta_{l'}}/\partial y$$

$$A_{33}^{(l')} = -2\partial\varphi_{\Delta_{l'}}/\partial z$$

$$A_{41}^{(l')} = 2\partial\ln|MG_{l'}B_{1,l'}^{(-)}|/\partial x \quad A_{42}^{(l')} = 2\partial\ln|MG_{l'}B_{1,l'}^{(-)}|/\partial y$$

$$A_{43}^{(l')} = 2\partial\ln|MG_{l'}B_{1,l'}^{(-)}|/\partial z$$

$$b_1^{(l)} = -\nabla^2\ln|B_{1,l}^{(+)}| - \nabla\ln|B_{1,l}^{(+)}|\cdot\nabla\ln|B_{1,l}^{(+)}| + \nabla\varphi_{\Sigma_l}\cdot\nabla\varphi_{\Sigma_l}$$

$$b_2^{(l)} = -2\nabla\ln|B_{1,l}^{(+)}|\cdot\nabla\varphi_{\Sigma_l} - \nabla^2\varphi_{\Sigma_l}$$

$$b_3^{(l')} = -\nabla^2\ln|MG_{l'}B_{1,l'}^{(-)}| - \nabla\ln|MG_{l'}B_{1,l'}^{(-)}|\cdot\nabla\ln|MG_{l'}B_{1,l'}^{(-)}| + \nabla\varphi_{\Delta_{l'}}\cdot\nabla\varphi_{\Delta_{l'}}$$

$$b_4^{(l')} = -2\nabla\ln|MG_{l'}B_{1,l'}^{(-)}|\cdot\nabla\varphi_{\Delta_{l'}} - \nabla^2\varphi_{\Delta_{l'}}$$

A full system of matrix equations can be composed of concatenated blocks of the form of Eq. (S11), with one block taking the form of the top two rows for each transmit coil l, and one block taking the form of the bottom two rows for each receive coil l'.

Eq. (S11) can be solved directly with a constrained nonlinear optimization procedure of choice. Note, however, that all nonlinearities in Eq. (S11) can be associated with constant (e.g., indeed unit) matrix elements. Thus, they can be removed by appropriate recombination of the rows or columns of the matrix A. Pairwise subtraction of rows associated with different coils, or subtraction of the row associated with a common reference coil combination from each existing row, and removal of unknowns with vanishing coefficients can, results in the simplified system of equations, which can be, for example:

$$\overbrace{\begin{bmatrix} A_{11}^{(lm)} & A_{12}^{(lm)} & A_{13}^{(lm)} & 0 & 0 & 0 \\ A_{21}^{(lm)} & A_{22}^{(lm)} & A_{23}^{(lm)} & 0 & 0 & 0 \\ A_{31}^{(l'm')} & A_{32}^{(l'm')} & A_{33}^{(l'm')} & -A_{41}^{(l'm')} & -A_{42}^{(l'm')} & -A_{43}^{(l'm')} \\ A_{41}^{(l'm')} & A_{42}^{(l'm')} & A_{43}^{(l'm')} & A_{31}^{(l'm')} & A_{32}^{(l'm')} & A_{33}^{(l'm')} \end{bmatrix}}^{A^{sub}} \quad \text{(S11)}$$

$$\overbrace{\begin{bmatrix} \partial\varphi_0/\partial x \\ \partial\varphi_0/\partial y \\ \partial\varphi_0/\partial z \\ \partial\ln|M|/\partial x \\ \partial\ln|M|/\partial y \\ \partial\ln|M|/\partial z \end{bmatrix}}^{x^{sub}} = \overbrace{\begin{bmatrix} b_1^{(lm)} \\ b_2^{(lm)} \\ b_3^{(l'm')} \\ b_4^{(l'm')} \end{bmatrix}}^{b^{sub}}$$

In Eq. (S13), $A_{jk}^{(lm)} \equiv A_{jk}^{(l)} - A_{jk}^{(m)}$ and $b_j^{(lm)} \equiv b_j^{(l)} - b_j^{(m)}$. The subtraction operation can also remove reference to the electrical properties σ and ∈. However, the purely linear Eq. (S13) for $\nabla\phi_0$ and $\nabla\ln|M|$ can be solved using a simple matrix inverse, for example, a Moore-Penrose pseudoinverse with standard regularization approaches. Local values of $\nabla\phi_0$ and $\nabla\ln|M|$ can then be inserted into Eq. (S11), yielding solutions for the electrical property values and the remaining local derivative unknowns in a second linear stage via the following equation:

$$\overbrace{\begin{bmatrix} 0 & 0 & 1 & 0 \\ -1 & 0 & 0 & 1 \\ 0 & 0 & 1 & 0 \\ 1 & -1 & 0 & 1 \end{bmatrix}}^{\tilde{A}} \overbrace{\begin{bmatrix} \nabla^2\varphi_0 \\ \nabla^2\ln|M| \\ \omega^2\mu\varepsilon \\ \omega\mu\sigma \end{bmatrix}}^{\tilde{x}} = \overbrace{\begin{bmatrix} \tilde{b}_1^{(l)} \\ \tilde{b}_2^{(l)} \\ \tilde{b}_3^{(l')} \\ \tilde{b}_4^{(l')} \end{bmatrix}}^{\tilde{b}} \quad \text{(S14)}$$

For example, the right-hand side vector elements $\{\tilde{b}_1^{(l)}, \tilde{b}_2^{(l)}, \tilde{b}_3^{(l')}, \tilde{b}_4^{(l')}\}$ can combine all known terms involving $\nabla\phi_0$ and $\nabla\ln|M|$ with the original right-hand side terms $\{b_1^{(l)}, b_2^{(l)}, b_3^{(l')}, b_4^{(l')}\}$. This two-stage linear reconstruction strategy can be quite fast, and it can also provide valuable insight into the fundamental needs and/or preferences for robust solution. For example, once first-stage gradients can be computed, the equations involving permittivity and conductivity can be uncoupled. Exemplary permittivity can be determined by a substitution after the gradients $\nabla\phi_0$ and $\nabla\ln|M|$ can be known, and thus it can be computed from transmit equations alone, from receive equations alone (e.g., as long as at least one transmit map can be available to compute $|MG_1B_{1,l'}^{(-)}|$ from the MR signals), or from both together.

From the second-stage Eq. (S14), however, it can be clear that transmit as well as receive equations can be needed or used to render the system of equations for conductivity nonsingular. It can be the conjugate relationship of the transmit and the receive field phase to the common phase reference which can facilitate a unique and purely local solution: the opposite signs of the unknown phase terms in Eqs. (4) and (5) can result in opposite signs of coefficients in Eq. (S14), and any deviation from truth in $\nabla^2\phi_0$ can create oppositely-directed errors in transmit and receive equations. Alternatively, the need for transmit-receive balance in conductivity mapping can be eliminated by taking second-pass divergences of derived phase and magnetization gradients to compute $\nabla^2\phi_0$ and $\nabla^2\ln|M|$ directly. This approach can sacrifice locality and some degree of robustness (e.g., since additional derivatives of the derived quantities $\Delta\phi_0$ and $\nabla\ln|M|$ can be needed) in exchange for the convenience of using a smaller number of coils and time-consuming field maps. In either exemplary approach, the accounting of equations and unknowns can be straightforward. For the general formulation in which both transmit and receive equations can be used, there can be ten real unknowns, or eight real unknowns if $\nabla^2\phi_0$ and $\nabla^2\ln|M|$ can be assumed to be derivable from $\nabla\phi_0$ and $\nabla\ln|M|$. There can be two real equations for each transmit coil or each receive coil, respectively. Thus, either four or five independent coils including at least one transmit and at least one receive coil can be needed for a unique solution. A two- to three-element transmit-receive array can suffice in any case, and addition of more array elements can improve overdetermination and robustness.

Figure 11:
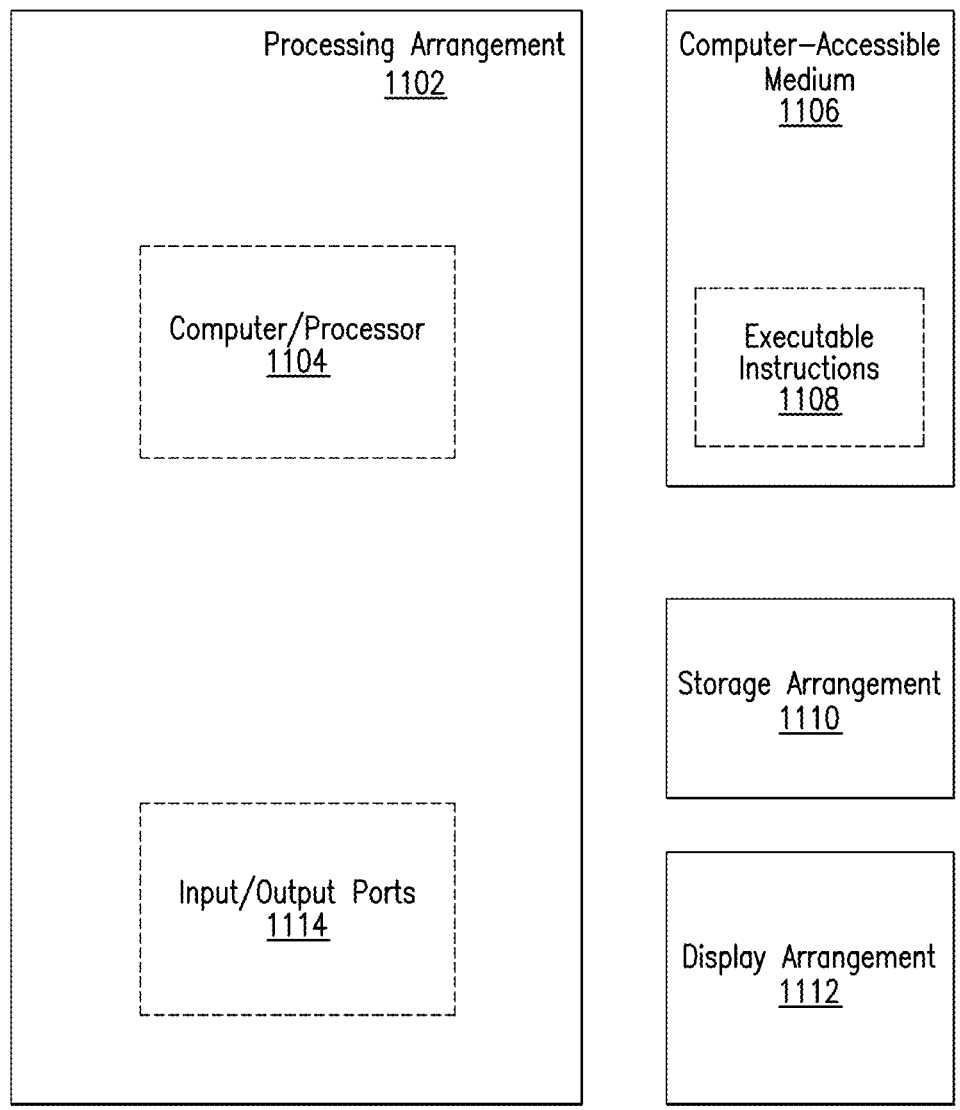
FIG. 11 is an exemplary a block diagram of an exemplary embodiment of a system according to the present disclosure.

FIG. 11 shows a block diagram of an exemplary embodiment of a system according to the present disclosure which can be used to utilize the exemplary methods, approaches, and techniques, including the exemplary LMT approach/procedure described herein. For example, exemplary procedures in accordance with the present disclosure described herein can be performed by a processing arrangement and/or a computing arrangement 1102. Such processing/computing arrangement 11002 can be, for example, entirely or a part of, or include, but not limited to, a computer/processor 1104 that can include, for example, one or more microprocessors, and use instructions stored on a computer-accessible medium (e.g., RAM, ROM, hard drive, or other storage device).

As shown in FIG. 11, for example, a computer-accessible medium 1106 (e.g., as described herein above, a storage device such as a hard disk, floppy disk, memory stick, CD-ROM, RAM, ROM, etc., or a collection thereof) can be provided (e.g., in communication with the processing arrangement 1102). The computer-accessible medium 1106 can contain executable instructions 1108 thereon. In addition or alternatively, a storage arrangement 1110 can be provided separately from the computer-accessible medium 1106, which can provide the instructions to the processing arrangement 1102 so as to configure the processing arrangement to execute certain exemplary procedures, processes, and methods, as described herein above, for example.

Further, the exemplary processing arrangement 1102 can be provided with or include an input/output arrangement 1114, which can include, for example, a wired network, a wireless network, the internet, an intranet, a data collection probe, a sensor, etc. As shown in FIG. 3, the exemplary processing arrangement 1102 can be in communication with an exemplary display arrangement 1112, which, according to certain exemplary embodiments of the present disclosure, can be a touch-screen configured for inputting information to the processing arrangement in addition to outputting information from the processing arrangement, for example. Further, the exemplary display 1112 and/or a storage arrangement 1110 can be used to display and/or store data in a user-accessible format and/or user-readable format.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. Various different exemplary embodiments can be used together with one another, as well as interchangeably therewith, as should be understood by those having ordinary skill in the art. In addition, certain terms used in the present disclosure, including the specification, drawings and claims thereof, can be used synonymously in certain instances, including, but not limited to, for example, data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it is explicitly incorporated herein in its entirety. All publications referenced are incorporated herein by reference in their entireties.

EXEMPLARY REFERENCES

The following references are hereby incorporated by reference in their entirety.

[1] Sodickson, D. K., et. al. ISMRM 2012, 387.
[2] Katscher, U., et. al. *IEEE Trans Med Imagining*, 2009, 28:1365. Alon, L. et. al. ISMRM 2013, 2519.
[3] Geddes, L. A. & Baker, L. E. The specific resistance of biological material—a compendium of data for the biomedical engineer and physiologist. *Med Biol Eng* 5, 271-293 (1967).
[4] Gabriel, S., Lau, R. W. & Gabriel, C. The dielectric properties of biological tissues: II. Measurements in the frequency range 10 Hz to 20 GHz. *Phys Med Biol* 41, 2251-2269 (1996).
[5] Joines, W. T., Zhang, Y., Li, C. & Jirtle, R. L. The measured electrical properties of normal and malignant human tissues from 50 to 900 MHz. *Med Phys* 21, 547-550 (1994).
[6] Metherall, P., Barber, D. C., Smallwood, R. H. & Brown, B. H. Three-dimensional electrical impedance tomography. *Nature* 380, 509-512 (1996).
[7] Newell, J. C., Isaacson, D. & Mueller, J. L. Special Issue on Electrical Impedance Imaging. *IEEE Trans Med Imaging* 21, 553-554 (2002).
[8] Lauterbur, P. Image formation by induced local interactions: examples employing nuclear magnetic resonance. *Nature* 242, 190-191 (1973).
[9] Wiesinger, F., Seifert, F., Koenig, H. & Pruessmann, K. P. in *Morning Course on Unsolved Problems and Unmet Needs in Magnetic Resonance, 13th Scientific Meeting, International Society for Magnetic Resonance in Medicine.*
[10] Katscher, U. et al. Determination of electric conductivity and local SAR via B1 mapping. *IEEE Trans Med Imaging* 28, 1365-1374, doi:10.1109/TMI.2009.2015757 (2009).
[11] Katscher, U., Findeklee, C. & Voigt, T. B(1)-based specific energy absorption rate determination for non-quadrature radiofrequency excitation. *Magn Reson Med*, doi:10.1002/mrm.24215 (2012).
[12] Zhang, X., de Moortele, P. F., Schmitter, S. & He, B. Complex B(1) mapping and electrical properties imaging of the human brain using a 16-channel transceiver coil at 7 T. *Magn Reson Med*, doi:10.1002/mrm.24358 (2012).
[13] Hoult, D. I. The Principle of Reciprocity in Signal Strength Calculations—A Mathematical Guide. *Concepts Magn Reson* 12, 173-187 (2000).

What is claimed is:

1. A method for determining at least one property of at least one target, comprising:
   determining electromagnetic-field-related quantities associated with signals provided from the at least one target from at least one transmit pattern and at least one receive pattern;
   providing the electromagnetic-field-related quantities to procedures to relate the electromagnetic-field-related quantities to (i) a plurality of unknown electrical property values of the at least one target, and (ii) a plurality of residual field-related unknown values of the at least one target;
   determining (i) the unknown electrical property values of the at least one target, and (ii) the residual field-related unknown values of the at least one target from a unique solution to at least one expression that is derived from the at least one transmit pattern and the at least one receive pattern, wherein the at least one expression includes only transverse components;
   eliminating non-transverse components using at least one of (i) combinations of a plurality of expressions or (ii) at least one relation governing a behavior of electromagnetic fields; and
   determining the at least one property of the at least one target based on (i) the unknown electrical property values of the at least one target, and (ii) the residual field-related unknown values of the at least one target.

2. The method of claim 1, wherein the at least one transmit pattern is based on a spatial distribution of a magnetic field used for a signal excitation, and wherein the at least one receive pattern is based on a distribution of a signal sensitivity in at least one receiving element.

3. The method of claim 1, wherein the at least one relation includes Gauss's law.

4. The method of claim 1, wherein the at least one target includes at least one material.

5. The method of claim 4, wherein the at least one material (i) has a plurality of anisotropic electrical property tensors, (ii) has a plurality of scalar properties with a non-vanishing electrical property gradient or (iii) includes at least one tissue.

6. The method of claim 1, wherein the residual field-related unknown values include at least one value derived from an absolute phase of an electromagnetic field.

7. The method of claim 1, wherein the at least one property is at least one of at least one electrical property or at least one partial cross-sectional property.

8. A non-transitory computer-accessible medium having stored thereon computer-executable instructions provided for determining at least one property of at least one target, when a computer arrangement executes the instructions, the computer arrangement is configured to perform procedures comprising:
  determining electromagnetic-field-related quantities associated with signals provided from the at least one target from at least one transmit pattern and at least one receive pattern;
  providing the electromagnetic-field-related quantities to procedures to relate the electromagnetic-field-related quantities to (i) a plurality of unknown electrical property values of the at least one target, and (ii) a plurality of residual field-related unknown values of the at least one target;
  determining (i) the unknown electrical property values of the at least one target, and (ii) the residual field-related unknown values of the at least one target from a unique solution to at least one expression that is derived from the at least one transmit pattern and the at least one receive pattern, wherein the at least one expression includes only transverse components;
  eliminating non-transverse components using at least one of (i) combinations of a plurality of expressions or (ii) at least one relation governing a behavior of electromagnetic fields; and
  determining the at least one property of the at least one target based on (i) the unknown electrical property values of the at least one target, and (ii) the residual field-related unknown values of the at least one target.

9. The computer-accessible medium of claim 8, wherein the at least one transmit pattern is based on a spatial distribution of a magnetic field used for a signal excitation, and wherein the at least one receive pattern is based on distribution of a signal sensitivity in a receiving element.

10. The computer-accessible medium of claim 8, wherein the at least one relation includes Gauss's law.

11. The computer-accessible medium of claim 8, wherein the at least one target includes at least one material.

12. The computer-accessible medium of claim 11, wherein the at least one material (ii) has a plurality of anisotropic electrical property tensors, (ii) has a plurality of scalar properties with a non-vanishing electrical property gradient, or (iii) includes at least one tissue.

13. The computer-accessible medium of claim 8, wherein residual field-related unknown values include at least one value derived from an absolute phase of an electromagnetic field.

14. The computer-accessible medium of claim 8, wherein the at least one property is at least one of at least one electrical property or at least one partial cross-sectional property.

15. A system for determining at least property of at least one target, comprising: a computer hardware arrangement configured to:
  a. determine electromagnetic-field-related quantities associated with signals provided from the at least one target from at least one transmit pattern and at least one receive pattern,
  b. provide the electromagnetic-field-related quantities to procedures to relate the electromagnetic-field-related quantities to (i) a plurality of unknown electrical property values of the at least one target, and (ii) a plurality of residual field-related unknown values of the at least one target,
  c. determine (i) the unknown electrical property values of the at least one target, and (ii) the residual field-related unknown values of the at least one target from a unique solution to at least one expression that is derived from the at least one transmit pattern and the at least one receive pattern, wherein the at least one expression includes only transverse components;
  d. eliminate non-transverse components using at least one of (i) combinations of a plurality of expressions or (ii) at least one relation governing a behavior of electromagnetic fields, and
  e. determine the at least one property of the at least one target based on (i) the unknown electrical property values of the at least one target, and (ii) the residual field-related unknown values of the at least one target.

16. The system of claim 15, wherein the at least one property is at least one of at least one electrical property or at least one partial cross-sectional property.

* * * * *